US00PP12966P2

(12) United States Plant Patent
Bunker

(10) Patent No.: US PP12,966 P2
(45) Date of Patent: Sep. 17, 2002

(54) BRACTEANTHA PLANT NAMED 'REDBRAPIN'

(75) Inventor: Kerry Veianne Bunker, Redland Bay (AU)

(73) Assignee: Redlands Nursery Pty. Ltd., Redland Bay (AU)

( * ) Notice: Subject to any disclaimer, the term of this patent is extended or adjusted under 35 U.S.C. 154(b) by 18 days.

(21) Appl. No.: 09/844,367

(22) Filed: Apr. 30, 2001

(51) Int. Cl.[7] ..... A01H 5/00
(52) U.S. Cl. ..... Plt./359
(58) Field of Search ..... Plt./359

(56) References Cited

PUBLICATIONS

UPOV–ROM GTITM Computer Database, 2001/06, GTI Jouve Retrieval Software, citation for 'Redbrapin'.*

* cited by examiner

*Primary Examiner*—Bruce R. Campell
*Assistant Examiner*—Susan B. McCormick
(74) *Attorney, Agent, or Firm*—C. A. Whealy

(57) ABSTRACT

A new and distinct cultivar of Bracteantha plant named 'Redbrapin', characterized by its compact and bushy growth habit; upright, outwardly spreading and rounded plant form; freely-flowering habit; dark pink-colored involucral bracts and orange-colored disc florets; and short and strong peduncles that hold inflorescences above the foliage.

1 Drawing Sheet

BACKGROUND OF THE INVENTION

The present invention relates to a new and distinct cultivar of Bracteantha plant, botanically known as *Bracteantha bracteata* and referred to by the name 'Redbrapin'.

The new Bracteantha is a product of a planned breeding program conducted by the Inventor in Redland Bay, Queensland, Australia. The objective of the program is to create and develop Bracteantha cultivars with a compact growth habit; numerous inflorescences with attractive involucral bract coloration, and long-lasting inflorescences.

The new Bracteantha originated from a cross by the Inventor of a proprietary selection of *Bracteantha bracteata* identified as code number 95-137, not patented, as the female, or seed, parent with a proprietary selection of *Bracteantha bracteata* identified as code number 95-155, not patented, as the male, or pollen parent. The new Bracteantha was discovered and selected by the Inventor as a plant within the progeny of the stated cross in a controlled environment in Redland Bay, Queensland, Australia in 1997. The selection of the new Bracteantha was based on its dark pink-colored involucral bracts and compact growth habit.

Asexual reproduction of the new Bracteantha by terminal cuttings taken in a controlled environment in Redland Bay, Queensland, Australia, has shown that the unique features of this new Bracteantha are stable and reproduced true to type in successive generations.

The new Bracteantha has not been observed under all possible environmental conditions. The phenotype may vary somewhat with variations in environment such as temperature, daylength, light intensity, photoperiod, and water and nutritional status without, however, any variance in genotype.

The following characteristics have been repeatedly observed and are determined to be basic charactertistics of 'Redbrapin' and distinguish the new Bracteantha as a new and distinct cultivar:

1. Compact and bushy growth habit.

2. Upright, outwardly spreading and rounded plant form.

3. Freely-flowering habit.

4. Dark pink-colored involucral bracts and orange-colored disc florets.

5. Short and strong peduncles that hold inflorescences above the foliage.

Plants of the new Bracteantha can be compared to plants of the female parent, the selection 95-137. In side-by-side comparisons conducted by the Inventor in Redland Bay, Queensland, Australia, plants of the new Bracteantha differed from plants of the selection 95-137 in the following characteristics:

1. Inflorescence shape of the new Bracteantha is star-shaped whereas inflorescence shape of the selection 95-137 is rounded.

2. Inflorescences of the new Bracteantha have fewer involucral bracts than inflorescences of the selection 95-137.

3. Inflorescences of the new Bracteantha have dark pink-colored involucral bracts whereas inflorescences of the selection 95-137 have pale pink-colored involucral bracts.

Plants of the new Bracteantha can be compared to plants of the males parent, the selection 95-155. In side-by-side comparisons conducted by the Inventor in Redland Bay, Queensland, Australia, plants of the new Bracteantha differed from plants of the selection 95-155 in the following characteristics:

1. Growth habit of the new Bracteantha is compact and bushy whereas growth habit of the selection 95-155 is upright and open.

2. Inflorescences of the new Bracteantha have dark pink-colored involucral bracts whereas inflorescences of the selection 95-155 have red-colored involucral bracts.

Plants of the new Bracteantha can also be compared to plants of the cultivar Florabella Elizabeth, not patented. In side-by-side comparisons conducted by the Inventor in Redland Bay, Queensland, Australia, plants of the new Bracteantha differed from plants of the cultivar Florabella Elizabeth in the following characteristics:

1. Plants of the new Bracteantha are more compact than plants of the cultivar Florabella Elizabeth.

2. Inflorescence shape of the new Bracteantha is star-shaped whereas inflorescence shape of the cultivar Florabella Elizabeth is rounded.

3. Plants of the new Bracteantha have larger inflorescences than plants of the cultivar Florabella Elizabeth.

4. Plants of the new Bracteantha have shorter peduncles than plants of the cultivar Florabella Elizabeth.

Plants of the new Bracteantha differ primarily from plants of the cultivar Redbragol, U.S. Plant patent application Ser. No. 09/844,369, filed concurrently, in involucral coloration as plants of the cultivar Redbragol have bright yellow-colored involucral bracts.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new Bracteantha.

The photograph at the top of the sheet comprises a side perspective view of a typical plant of 'Redbrapin' grown in a 15-cm container for about 8 weeks.

The photograph at the bottom of the sheet comprises a close-up view of a typical inflorescence of 'Redbrapin'.

DETAILED BOTANICAL DESCRIPTION

The following observations, measurements and values describe plants grown in Redland Bay, Queensland, Australia, under outdoor conditions with day temperatures ranging from 20 to 30° C. and night temperatures ranging from 10 to 15° C. Rooted liners of the new Bracteantha were planted in 15-cm containers and grown for about 8 weeks. Color references are made to The Royal Horticultural Society Colour Chart, 1995 edition, except where general terms of ordinary dictionary significance are used.

Botanical classification: *Bracteantha bracteata* cultivar Redbrapin.

Parentage:

*Female or seed parent.*—Proprietary selection of *Bracteantha bracteata* identified as code number 95-137, not patented.

*Male or pollen parent.*—Proprietary selection of *Bracteantha bracteata*, identified as code number 95-155, not patented.

Propagation:

*Type.*—By cuttings.

*Time to initiate roots.*—Summer: About 7 days at 30° C. Winter: About 14 days at 20° C.

*Time to produce a rooted cutting.*—Summer: About 21 days at 30° C. Winter: About 28 days at 20° C.

*Root description.*—Fine to fibrous; freely-branching.

Plant description:

*General appearance.*—Compact and bushy growth habit; upright, outwardly spreading and rounded plant form with dense foliage and inflorescences held above the foliage on strong peduncles. Freely branching, about 33 lateral branches per plant. Appropriate for 15-cm containers.

*Crop time.*—Rapid growth rate; to produce a finished 15-cm containerized plant from rooted cuttings, about 8 weeks are required.

*Plant height.*—About 21 cm.

*Plant width.*—About 23.5 cm.

*Lateral branch description.*—Length: About 11.5 cm. Width: About 3.9 mm. Internode length: About 1.61 cm. Texture: Slightly pubescent. Color: 143C.

*Foliage description.*—Arrangement: Alternate, single, sessile. Quantity of leaves per lateral branch: About 21. Length: About 7.3 cm. Width: About 1.38 cm. Shape: Linear elliptic. Margin: Entire. Apex: Acute. Texture, both surfaces: Leathery; smooth, glabrous. Venation pattern: Narrowly arcuate to reticulate. Color: Young and fully expanded leaves, upper surface: 137A; venation, 144D. Young and fully expanded leaves, lower surface: 137C; venation, 144D.

Flowering description:

*Inflorescene form.*—Daisy-type composite inflorescence form. Inflorescences arranged acropetally on a capitulum. Inflorescences, star-shaped.

*Inflorescence longevity.*—Inflorescences last on the plant for about 21 days. Inflorescences persistent.

*Natural flowering season.*—Natural flowering season is year-round in Redland Bay, Queensland, Australia; flowering continuous.

*Quantity of inflorescences.*—One terminal inflorescence per lateral branch, about 33 inflorescences per plant.

*Inflorescence aspect.*—Flat.

*Inflorescence diameter.*—About 4.62 cm.

*Inflorescence depth (height).*—About 1.76 cm.

*Disc diameter.*—About 1.26 cm.

*Fragrance.*—Slight, mild; sweet.

*Involucral bracts.*—Quantity per inflorescence: About 78 in multiple whorls. Length: About 1.54 cm. Width: About 4.6 mm. Shape: Ligulate, concave. Apex: Acute. Base: Truncate. Margin: Entire. Texture, both surfaces: Smooth, papery, hard, satiny. Aspect: Mostly flat; perpendicular to the peduncle. Color: When opening and fully opened, upper surface: Inner whorls: 63C. Central whorls: 63B. Outer whorls: 63A. When opening and fully opened, lower surface: Inner whorls: 61A. Outer whorls: 63A.

*Disc florets.*—One inconspicuous whorl of female filiform florets surround the perimeter of the disc, remainder of disc covered with bisexual disc florets. Quantity per inflorescence: About 487. Shape: Tubular with five lobes. Length: About 8.6 mm. Width: About 0.9 mm. Color: Immature: 23B. Mature: 24B.

*Peduncle.*—Length: About 4.66 cm. Diameter: About 2.9 mm. Aspect: Erect. Strength: Strong. Texture: Slightly pubescent. Color: 143C.

*Inflorescence bud.*—Length: About 1.9 cm. Diameter: About 1.72 cm. Shape: Broadly ovoid with acute apex. Color: 61A.

*Androecium.*—Present only on disc florets. Stamen quantity/arrangement: Fused anther tube with 5 long thin linear anthers surrounding the style. Anther color: 23A. Amount of pollen: Abundant. Pollen color: Yellow.

*Gynoecium.*—Present on both filiform and disc florets. Pistil number: One per floret. Style color: 23A. Stigma shape: Bi-parted. Stigma color: 23A.

*Seed.*—Length: About 1.75 mm. Diameter: About 0.73 mm. Color: 177B.

Disease/pest resistance: Plants of the new Bracteantha have not been observed to be resistant to pathogens or pests common to Bracteantha.

It is claimed:

1. A new and distinct cultivar of Bracteantha plant named 'Redbrapin', as illustrated and described.

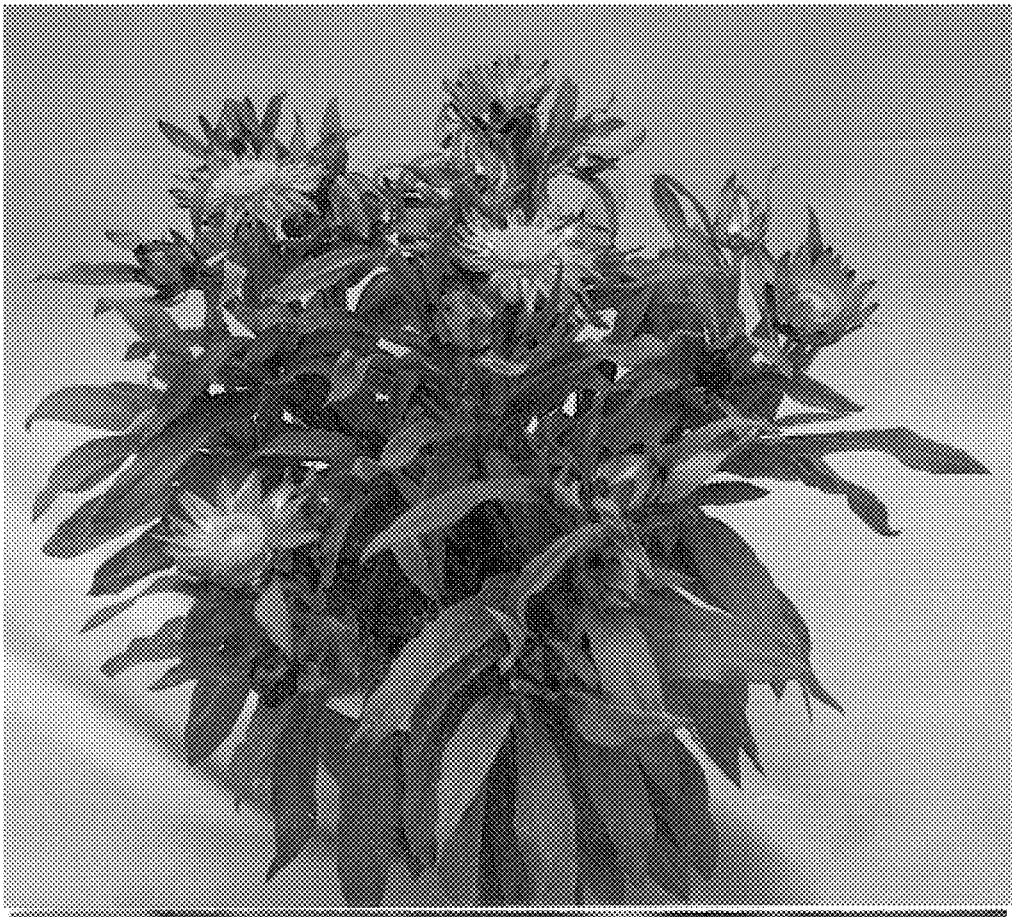
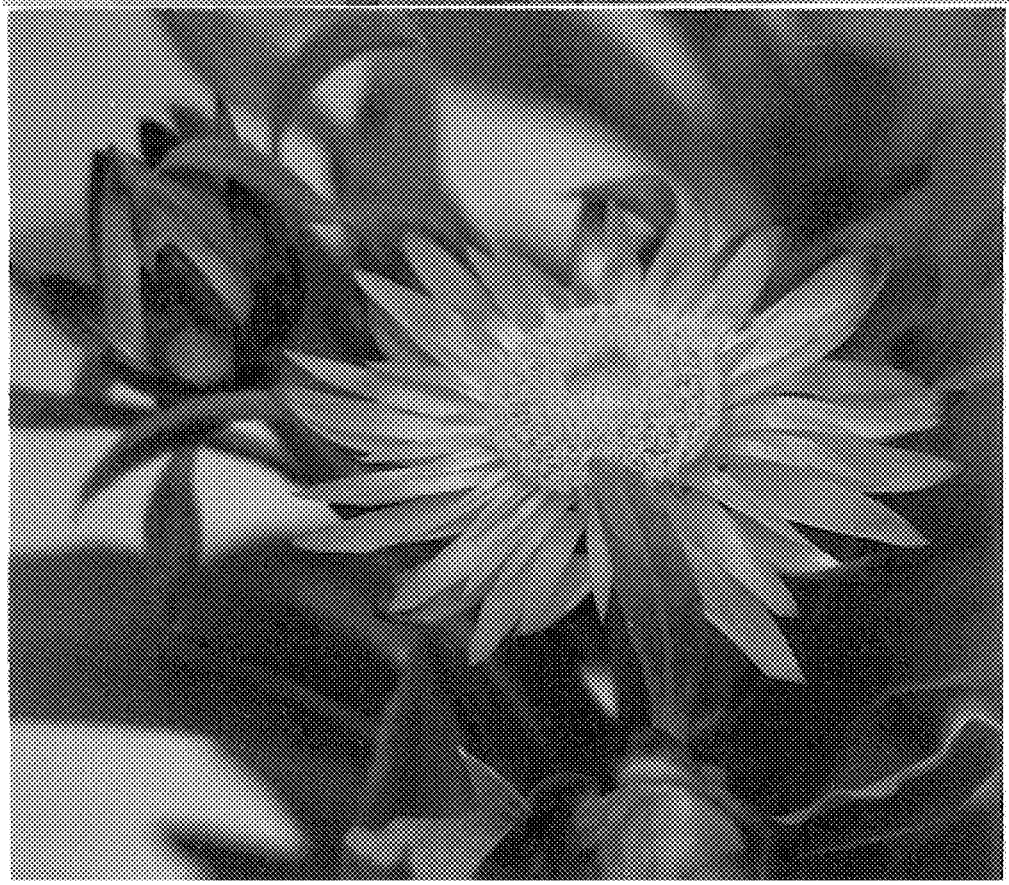

* * * * *